United States Patent [19]

Lahanas et al.

[11] Patent Number: 5,304,334
[45] Date of Patent: Apr. 19, 1994

[54] METHOD OF PREPARING A MULTIPHASE COMPOSITION

[75] Inventors: Konstantinos M. Lahanas, Hackensack, N.J.; Tracy N. Keeler, Northport, N.Y.; Andrew J. Bevacqua, East Setauket, N.J.; George Cioca, Lake Grove, N.Y.

[73] Assignee: Estee Lauder, Inc., New York, N.Y.

[21] Appl. No.: 874,933

[22] Filed: Apr. 28, 1992

[51] Int. Cl.$^5$ ............... A61K 31/78; A61K 31/785; B01J 13/00; C09K 19/36
[52] U.S. Cl. ................ 252/314; 252/299.7; 252/308; 252/309; 252/315.1; 252/315.3; 252/315.4; 424/78.03; 514/847; 514/937; 514/944
[58] Field of Search ........... 252/299.7, 308, 309, 252/314, 315.2, 315.3, 315.4, 315.1; 424/78.03; 514/847, 937, 944

[56] References Cited

U.S. PATENT DOCUMENTS

| | | | |
|---|---|---|---|
| 4,592,934 | 6/1986 | Wolstoncroft | 106/3 X |
| 4,604,281 | 8/1986 | Deckner et al. | 514/847 X |
| 4,720,353 | 1/1988 | Bell | 252/309 |
| 4,803,067 | 2/1989 | Brunetta et al. | 514/944 X |
| 4,859,753 | 8/1989 | Gallot et al. | 252/315.1 X |
| 4,883,659 | 11/1989 | Goodman et al. | 424/78.03 |
| 4,954,332 | 9/1990 | Bissett et al. | 514/847 X |
| 4,966,205 | 10/1990 | Tanaka | 141/9 |
| 5,015,469 | 5/1991 | Yoneyama et al. | 252/308 X |
| 5,061,481 | 10/1991 | Suzuki et al. | 514/937 X |

FOREIGN PATENT DOCUMENTS 0076146 4/1983 European Pat. Off. ......... 424/78.03

OTHER PUBLICATIONS

A. Bevacqua, K. Lahanas; I. Cohen; G. Cioca; *Liquid Crystals in Multiple Emulsions*; Cosmetics & Toiletries; vol. 106, May 1991; pp. 53-56.

*Primary Examiner*—Richard D. Lovering
*Attorney, Agent, or Firm*—Pennie & Edmonds

[57] ABSTRACT

The instant invention relates to methods of preparing and stabilizing complex multiphase compositions that include distinct phases of water, gel, liquid crystal or oil and perfluoropolyether dispersed in a continuous phase of a silicone fluid. In particular, the present invention relates to a method of preparing a stable multiphase composition comprising the steps of mixing an aqueous solution of a water-soluble polymeric emulsifier, a silicone-based emulsifier and an oleophobic, hydrophobic silicone fluid in amounts effective to form a stable water-in-silicone emulsion; mixing the water-in-silicone emulsion with a hydrophilic gel comprising a homogeneous mixture of water and a sufficient amount of at least one viscosity-enhancing, water-soluble polymer, the emulsion and gel being combined in amounts effective to form a dispersion in which the gel is dispersed in the emulsion; and adding to the dispersion an oil or a thermotropic liquid crystal and a perfluoropolyether in amounts effective to form a stable, multiphase composition comprising a continuous phase of silicone fluid and independent, polydisperse phases of water, gel, oil or liquid crystal and perfluoropolyether.

27 Claims, 4 Drawing Sheets

METHOD OF PREPARING A MULTIPHASE COMPOSITION

TABLE OF CONTENTS

1. FIELD OF THE INVENTION
2. BACKGROUND OF THE INVENTION
   2.1 EMULSIONS
      2.1.1 SIMPLE EMULSIONS
      2.1.2 EMULSIONS CONTAINING PERFLUOROPOLYETHER
      2.1.3 STABILIZATION OF EMULSION BY PERFLUOROPOLYETHER
      2.1.4 EMULSIONS CONTAINING SILICONE
      2.1.5 EMULSIONS CONTAINING OIL
      2.1.6 EMULSIONS CONTAINING LIQUID CRYSTALS
      2.1.7 THREE, FOUR AND FIVE PHASE EMULSIONS
   2.2 PROPERTIES OF EMULSIONS
      2.2.1 MULTIPLE PHASE EMULSIONS TAILOR DELIVERY
      2.2.2 PHASE INVERSION IN MULTIPHASE EMULSIONS
3. SUMMARY OF THE INVENTION
4. BRIEF DESCRIPTION OF THE DRAWINGS
5. DETAILED DESCRIPTION OF THE INVENTION
   5.1 PREPARATION OF FIVE PHASE EMULSION
      5.1.1 EXAMPLE ONE
      5.1.2 EXAMPLE TWO
      5.1.3 EXAMPLE THREE
      5.1.4 PHOTOMICROSCOPY
      5.1.5 NUMBER OF WATER PHASES
      5.1.6 DILUTION EXPERIMENTS - LOCATION OF SILICONE PHASE
      5.1.7 DETERMINATION OF POSITIONS OF REMAINING PHASES
   5.2 TEST OF CHANGES DUE TO PRODUCT PRESSURE SENSITIVITY
   5.3 TEST FOR SHORT AND LONG-TERM MOISTURIZATION
CLAIMS
ABSTRACT

1. FIELD OF THE INVENTION

The present invention is a novel method of preparing a multiphase composition for use in dermatology and cosmetics. In particular, the present invention relates to a method of preparing a complex emulsion comprising a continuous phase of a silicone fluid and independent dispersed phases comprising a gel phase, a secondary water phase, both of which aqueous phases can release bioavailable water-soluble ingredients, a perfluoropolyether phase, and an oil or liquid crystal phase that can carry and release bioavailable lipid-soluble ingredients.

2. BACKGROUND OF THE INVENTION

Conventional cosmetic vehicles for skin moisturization deliver moisture to the skin only on the initial application of the cosmetic moisturizer. The need for a cosmetic, dermatologic or medicinal multiphasic vehicle that will, in addition, provide sustained skin moisturization while blocking skin moisture loss has been long felt. There has also been a need for a multiphasic vehicle that can be used to provide water- soluble and lipid-soluble active ingredients, such as vitamins, plant extracts, antioxidants, proteins, polymers, oils and the like. Most cosmetic vehicles consist of emulsions.

2.1 EMULSIONS

2.1.1 Simple Emulsions

An emulsion is known to be a dispersed system comprising at least two immiscible liquid phases (*Remington's Pharmaceutical Sciences*, 18th Edition, 1990). The emulsion's immiscible liquid phase is composed of droplets between 0.005 to 2000 microns in diameter although the range of droplet diameters may be narrower (e.g., between 0.1 to 100 microns). Emulsions are known to be thermodynamically unstable. It is believed that the free energy associated with high surface area of small droplets is reduced when these droplets coalesce into large droplets of less surface area. To minimize droplet coalescence, it is known that an emulsifying agent can be added to form a thin film about each droplet of immiscible liquid in the emulsion (*Remington's Pharmaceutical Sciences*, 18th Edition, 298-309, 1990).

2.1.2 Emulsions Containing Perfluoropolyether

Perfluoropolyethers (PFPE) such as perfluoropolymethylisopropyl ether (Montefluos trade name Fomblin HC) are useful as non-greasy lubricants. These compounds are odorless, colorless, tasteless, nonvolatile, nontoxic, and chemically stable below 300° C. Consequently, PFPEs with a molecular weight between 250 to about 30,000 have been used in a wide variety of cosmetic formulations for make-up, hair, toiletry, skin and baby products (Brunetta F., et. al., *Cosmet. Toilet. Ital.* Edition 2, March/April 1986; Brunetta F., et al., *XIV Congreso I.F.S.C.C.* Barcelonea, Spain Volume 1:513, Sep. 16-19, 1986). The chemical formula of FOMBLIN HC is as follows:

$$CF_3-[(O-CF(CF_3)-CF_2)_n-(O-CF_2)_m]-CF_3$$

where $n=1$ to 40 and $m=1$ to 80. The perfluoromethylisopropyl ethers Fomblin HC/04, HC/25 or HC/R are commercially available (Bader S, et al., Montefluos SpA, Milan, Italy). The addition of substituent groups such as carboxylic acids, alcohols, esters, and the like to the carbons of PFPEs is known to increase the molecule's polarity, hydrophilicity or charge. Ordinarily, PFPEs are insoluble in polar or nonpolar solvents except for certain halogenated solvents, such as tetrachlorethane.

PFPEs are known additives to multiphase emulsions due to their tendency to form thin films. "Perfluoropolyethers For Cosmetics", *D&CI*, September 1988, 34-35, 116, 119, disclose the use of perfluoropolyethers (in particular, Fomblin) in cosmetics in which the insolubility of Fomblin is asserted not to affect the preparation of stable emulsions. It is further disclosed that the use of 0.1-3% Fomblin HC in oil-in-water emulsions produces finer dispersions and that 0.2-1.0% of Fomblin HC/25 increases the moisturizing properties of creams. Finally, the article states that all grades of Fomblin HC form a "thin and non-occlusive film, providing a satin finish and skin feel" (Ibid. at p. 119; see, also, Bader S, et al., Montefluos SpA Company bulletin). U.S. Pat. No. 4,803,067 discloses the utility of perfluoropolyethers not only as waterproofing agents but also as a barrier against loss of moisture from the skin without adversely affecting skin respiration.

It is also known that emulsions of PFPE can be used to protect human and animal skin against toxic agents such as mineral acids, caustic alkali, and organic solvents such as toluene and kerosene (Morganti P & Randazzo, *J. Appl. Cosmetol.* S.D. 7:23–30, 1989).

2.1.3 Stabilization of Emulsion by Perfluoropolyether

It is known that a three-phase emulsion containing perfluoropolyether can be made by pouring the PFPE and oil into water heated to 70° C. under vigorous mixing (Bader S, et al., Montefluos SpA Company bulletin). An oil-water emulsion lacking PFPE has larger droplets than the same emulsion containing PFPE (Bader S, et al., Montefluos SpA Company bulletin). Thus, one mode by which PFPE appears to stabilize a three phase emulsion is by decreasing the coalescence rate of the emulsion droplets. Due to the insolubility of PFPE in oil and water, it is generally expected that, in part, PFPE is dispersed as droplets among the oil-water droplets. Due to the tendency of PFPE to form films, some PFPE will be present as a thin film at the oil-water droplet interface.

The PFPE molecule is not in principle surface active due to its nonhydrophilic molecular structure. Also, its stabilizing activity cannot be explained by current theories for dispersed systems (Bader S, et al., Montefluos SpA Company bulletin).

The basis for the stabilization of oil-water emulsions by PFPE is not certain. One hypothesis is that the low surface tension of PFPE may allow a thin PFPE film to form over the oil droplets of a PFPE/oil/water multiphase emulsion, preventing the contact between drops necessary for droplet coalescence. Or, as an inert phase, PFPE may simply lower the collision frequency between emulsion droplets (Bader S, et al., Montefluos SpA Company bulletin). In addition, changes in the stability of an oil/water/PFPE multiphase emulsion can be expected if additional phases are added to the system.

2.1.4 Emulsions Containing Silicone

Stable emulsions containing silicones of two or three phases are well-known. The low surface tension of silicone promotes thin film formation which stabilizes emulsions. Lower alkyl ($C_1$–$C_4$) and amino-substituted polysiloxanes (silicones) are used because of their insolubility in polar and non-polar liquids such as water and oils. Seldom used are the cyclic silicones such as diphenylmethicone because of their oil solubility which causes the cyclic silicones to dissolve in the oil phase of the emulsion rather than forming a distinct phase.

Silicone emulsions have been used in a number of products. In cosmetic, pharmaceutical and skin preparations, a fat paste-like emulsion of decamethylpentasiloxane, poly(oxyethylene stearate), water and sorbitan monostearate has been used (Thimineur R. J. & Traver F. J., DE 3,045,083). In personal-care formulations, such as water-based hair conditioner, a water in silicone emulsion has been used (Gum, M. L., W085/03641/A1). In formulations for polishes an emulsion of a dimethylsiloxanes, naphtha hydrocarbons, emulsifiers and water has been used (Hill M. P. L. & Vandamme L. J. R., DE 3,616,575 A1). Water-thinned paint emulsions have used silicones (Udalova A. V., et al., *Lakokas Mater, Ikh. Primen.*, 2:14–16). Waterproof sealant emulsions have used silicones (Saad W. T. & Stodgell R. F., U.S. Pat. No. 4,383,062; Bauman T. M. & Freiberg A. L. U.S. Pat. No. 4,590,220).

U.S. Pat. No. 4,960,764 discloses multiphase composition having moisturizing characteristics which consists of a multiphase emulsion in which an oil-in-water emulsion is dispersed in a continuous phase of a silicone fluid with the aid of an effective dispersing amount of a second silicone fluid, in particular, dimethicone copolyol.

Surprisingly, silicone can be used to demulsify emulsions. Koerner G. & Schaefer D (U.S. Pat. No. 5,004,599) have employed a block copolymer combining polyoxyalkylene (having a surfactant-emulsifier function) and polysiloxane (having a silicone-emulsifier function) to successfully demulsify a crude oil/water emulsion.

2.1.5 Emulsions Containing Oil

Oils are common constituents of simple and multiple phase emulsions. In emulsions, the oils should not be surface active, detergent nor surfactant in activity. Otherwise, the oils can have nearly any chemical formula.

2.1.6 Emulsions Containing Liquid Crystals

The ordered phase of liquid crystals has many of the properties of the solid state such as optical anisotropy and birefringence which produce special interference patterns that can be detected using a cross polarizing microscope. Liquid crystals also have the mechanical properties of liquids. Because the crystals have only partial rotational or translational freedom the liquid crystals exist in a mesophase state (*Intro. to Liquid Crystals,* Priestly E. B., et al., editors, Plenum Press, N.Y. 1976).

Liquid crystals known as lyotropic liquid crystals may spontaneously form when the concentration of oils in an oil-water emulsion is at a particular concentration (See, e.g., Marland J. S. & Mulley B. A. *J. Pharm. Pharmacol.* 1971, 23(8): 561–572). Lyotropic liquid crystal formation is commonly observed in a wide variety of emulsions and such liquid crystals are known to be unstable.

There are liquid crystals that are known to form at only certain temperatures known as thermotropic liquid crystals. This type of liquid crystal is quite stable.

U.S. Pat. No. 4,999,348 discloses cosmetic and pharmaceutical compositions in which biologically active materials, such as Vitamin A, are enclosed in a cholesteric liquid crystal matrix, which, in turn, is dispersed in a "carrier" gel. Preferably, the carrier gel is a translucent or transparent polyacrylic gel. The compositions are disclosed as having a moisturizing effect on the skin, as well as the ability to relate vitamins in a controlled manner. Essentially the same disclosure is contained in "Liquid Crystals and Cosmetic Applications," Cioca, G. and Calvo, L. *Cosmet. & Toilet.* May 1990, 105, 57–62.

2.1.7 Three, Four and Five Phase Emulsions

It is known in theory, that a multiphase emulsion with "n" phases can be prepared through the remicellization of a multiphase emulsion with "n-1" phases. Each internal phase, in turn, may be polydisperse. Alternatively, multiphase emulsions have been formed by promoting phase inversions in simpler emulsion systems.

Three phase emulsions used in cosmetics such as the water/oil/water and oil/water/oil emulsions are well-known. The water/oil/water emulsion is prepared by redispersing a water-in-oil emulsion in an aqueous phase containing an oil-in-water emulsifier (de Luca M. *Cosm. Toilet.* 105:65–69, 1990). The physicochemical properties of three phase emulsions are well-established (Becher P., *Encyclopedia of Emulsion Technology* vol. 1:432–433, 1983).

Only a few four phase emulsions are known. Montefluos SpA (Milan, Italy) advertise a sunscreen lotion in their PFPE literature that contains water, dimethicone, PFPE, oils, and other polymers. This composition would form a four phase emulsion. A four phase emulsion was also reported by Bennett K. E., et al., (*J. Phys. Chem.* 86(20):3917–3919) using brine, hydrocarbon, alcohol, and alkylsulfonate sodium at certain mixtures and temperatures.

In addition, EP 0,319,638, published Jun. 14, 1989, discloses a multicomponent cosmetic composition containing liquid crystals, an aqueous gel carrier, silicone lubricants and various additives, including vitamins.

None of the foregoing references teach or suggest a method for the preparation of a multiphase composition comprising five distinct phases in which independent gel, water, oil or liquid crystal and perfluoropolyether phases are dispersed in a continuous phase of a silicone fluid. A method for the formation of such a stable five phase emulsion would be a novel and nonobvious invention.

2.2 PROPERTIES OF EMULSIONS

2.2.1 Multiple Phase Emulsions Tailor Delivery

In cosmetic emulsions that are applied to the skin, water and active ingredients ("actives") such as vitamins, oils, antioxidants and the like are released from their respective phases in the emulsion by diffusion. A product for external use having multiple discontinuous phases can serve a number of important functions. Each phase can function as an independent delivery system for moisturizers, emollients, bioactive materials, and the like. The release of material from the dispersed phase, and its subsequent absorption into the stratum corneum, are critically dependent on the interaction between the material, its solvent, and its immediate interface (Zatz J. L. & Cueman G. H. *J. Soc. Cosmet. Chem.* 39:211–222, 1988). The complexity of these interactions usually increases with the number of phases. This makes multiple emulsions excellent candidates for tailored-release systems, as exemplified by their use in the administration of vaccines, drugs, and anticancer agents (Becher P. *Encyclopedia of Emulsion Technology* pp. 199–202, Marcel Dekker, N.Y. 1985).

2.2.2 Phase Inversion in Multiphase Emulsions

Phase inversion occurs when an oil/water emulsion changes (inverts) to a water/oil emulsion. Inversion can be induced by adding electrolyte, changing the ratio of the phase volumes, cooling a heated emulsion, adjusting the amount of emulsifier, or when the dispersed phase exceeds 50% of the total volume of the emulsion (*Remington's Pharmaceutical Sciences*, pp 307–308, 1990).

3. SUMMARY OF THE INVENTION

The instant invention is directed to methods of preparing and stabilizing complex multiphase compositions that include distinct phases of water, gel, liquid crystal or oil and perfluoropolyether dispersed in a continuous phase of a silicone fluid. In particular, the present invention relates to a method of preparing a stable multiphase composition comprising the steps of mixing an aqueous solution of a water-soluble polymeric emulsifier, a silicone-based emulsifier and an oleophobic, hydrophobic silicone fluid in amounts effective to form a stable water-in-silicone emulsion; mixing the water-in-silicone emulsion with a hydrophilic gel comprising a homogeneous mixture of water and a sufficient amount of at least one viscosity-enhancing, water-soluble polymer, the emulsion and gel being combined in amounts effective to form a dispersion in which the gel is dispersed in the emulsion; and adding to the dispersion an oil or a thermotropic liquid crystal and a perfluoropolyether in amounts effective to form a stable, multiphase composition comprising a continuous phase of silicone fluid and independent, polydisperse phases of water, gel, oil or liquid crystal and perfluoropolyether.

In another embodiment of the present invention a method is disclosed of stabilizing a multiphase composition in which independent phases of water, gel, liquid crystal and perfluoropolyether are dispersed in a continuous phase of silicone fluid comprising adding an effective amount of a water-soluble polymeric emulsifier, or an aqueous solution thereof, to an aqueous mixture of an oleophobic, hydrophobic silicone fluid and a silicone-based emulsifier to form a stable water-in-oil emulsion. Upon formation of such a water-in-oil emulsion, the gel, liquid crystal and perfluoropolyether components are then added to complete the stabilized multiphase composition.

An object of the present invention also involves a method of preparing a complex multiphase composition in which a distinct oil phase is present in place of the liquid crystal. Like the liquid crystal component employed in the present method, the oil phase is capable of carrying and releasing lipid-soluble active ingredients to a surface, such as the skin, to which the multiphase composition is applied.

Another object of the present invention involves a method of preparing a complex multiphase composition in which a distinct gel phase, dispersed in the continuous silicone fluid phase of the "resting" multiphase composition, temporarily becomes the continuous phase under the "stressed" or "shearing" condition that obtains on application of the multiphase composition to a surface. Such a temporary phase inversion to a water/silicone/gel emulsion, allows the continuous gel phase to deliver a high initial dose of moisture to the surface. On removal of the externally applied pressure, i.e, after the multiphase composition has been applied, the composition reverts to its original "resting" state and is, subsequently, able to deliver a lower but sustained rate of moisturization to the surface.

Hence, yet another object of the present invention relates to providing a method of preparing a stable multiphase composition in which distinct hydrophilic gel and water phases are present which can carry and release water-soluble dermatologically or cosmetically active ingredients.

Moreover, the perfluoropolyether phase of the composition obtained by the present method forms a thin barrier across the surface, such as skin, which minimizes water loss from the surface while permitting natural skin respiration to take place substantially uninterrupted. Also, the dermatologically or cosmetically active lipid-soluble ingredient is preserved or maintained in the liquid crystal or oil phase until their release to the surface, such as skin.

5. DETAILED DESCRIPTION OF THE INVENTION

5.1 Preparation of Five Phase Emulsion

The order of combination of the five emulsion phases is not critical. Any order of combination will work. However, example one, below, represents the most preferred mode of formation of the emulsion.

5.1.1 Example One

Forming the Water-In-Silicone Emulsion. A water-in-silicone emulsion is formed by vigorous homogenization provided by a Silverson turboemulsifier with side mixing at room temperature. During vigorous continuous homogenization, a 1.5% aqueous solution of Hypan SS-201 is added in an amount equivalent to 11.25 weight percent of the final multiphase composition (hereafter, all percentages in parenthesis refer to the amount of the given component as a percent by weight of the final multiphase composition) to DC Q2-1403 (15.0%) and DC Q2-3225C (5.0%). Hypan SS-201 is a block copolymer of polyacrylamide and polyacrylonitrile. It has been discovered that other water-soluble polymeric emulsifiers can be used in place of the Hypan SS-201 such as, Pemulen TR-1, Pemulen TR-2, polyacrylamide, polyacrylonitrile, cellulosic thickeners, or methylvinyl ether/maleic anhydride copolymer crosslinked with 1,9-decadiene (i.e., Stabileze 06 from ISP Corp.). The water-soluble polymeric emulsifier is used to stabilize the water/silicone emulsion. DC Q2-1403 is dimethicone and dimethiconol, a Dow Corning silicone oil fluid consisting of dimethylsiloxane polymers (with variable percentages of high and low molecular weight polymer). DC Q2-3225C is also a Dow Corning product and consists of cyclomethicone/dimethicone copolyol (9/1, w/w). Similar silicone fluids and the like can be used in place of DC Q2-1403 and DC Q2-3225C, however, the cyclomethicones which are oil-soluble, should not be used in place of DC Q2-1403.

Perfluoropolyether. A perfluoropolyether (2.0%) is added to the water/silicone emulsion under vigorous continuous agitation. Perfluormethylisopropyl ether is the preferred PFPE. Examples of suitable PFPEs include, but are not limited to, Fomblin HC/04 (mean MW 1500), Fomblin HC/25 (mean MW 3200), and Fomblin HC/R (mean MW 6600), Montefluos Spa., Italy.

Gel Phase. The gel is preferably acid-neutralized, with a pH value between about 6.0 and about 8.0. The hydrophilic gel is neutralized with any suitable base, preferably an amine base. The most preferred base is TEA (triethanolamine, 1.0%). The gel may also include lactoderm (butylene glycol and mixed glyceride esters, 6%) and methylparaben (0.1%).

The gel is then added to the three phase emulsion of PFPE/water/silicone. In the emulsion, the water droplets within the continuous silicone phase are small compared to the water droplets in the bulk gel phase. The gel phase (35-55%, preferably 25.25%) is comprised primarily of viscosity-enhancing, water-soluble polymers (2-5 wt % in water) that are crosslinkable. Furthermore, these gelling agents may be neutral, anionic, cationic, or water-swelling. Examples of such polymeric gelling agents include, but are not limited to carbopol 940, carbomers polyacrylic acid, acrylate-based polymers, alginate-based polymers, methylcelluloses, locust bean polymer and the like. A second component, Lubrajel MS (18.0%), a mixture of polyglycerylmethylacrylate and propylene glycol, is preferably included in the gel phase.

The gel phase may contain any desired water-soluble cosmetically or dermatologically active ingredient such as:

Alogogen (an algae extract and marine protein);
Biofidelity Complex (an algae extract and yeast protein);
Procell (an algae extract and complex protein);
Actimoist EL (sodium hyalouronate);
Dermo Factor (tissue matrix extract);
Pantethine;
Root Protein Extract (Protein-glycoside complex);
Extract of Malvacae (Malvacae Extract);
Germall 115 (Imidazolidinyl urea, a preservative);
and electrolytes or salts to stabilize the polymers or modify the ionic strength of the gel. Water-soluble chelating agents, other botanical extracts, water-soluble vitamins, proteins, and the like may also be included.

Oil or Liquid Crystals. Oil of any kind may be added to the emulsion for the use of storing and release bioactive lipid-soluble substances. However, the oils should not have surface active, detergent or surfactant activity. Thermotropic liquid crystals can be added; preferably, the size of the crystals is conserved by gently sweeping them into the emulsion without vigorous agitation. The resulting multiphase composition is then stored in sealed glass containers to protect the quality of the composition.

5.1.2 Example Two

A water-in-silicone emulsion, such as that described in the preceding example, is prepared by mixing an about 0.5 to about 3 weight percent aqueous solution of an acrylamide copolymer (e.g., Hypan S5-201, about 5 to about 15 wt % of the total multiphase composition), a silicone-based emulsifier (e.g., a mixture of cyclomethicone and dimethiconol, 3-8 wt % of the total multiphase composition) and an oleophobic, hydrophobic silicone fluid, such as dimethicone, dimethiconol, or mixtures thereof (about 10-20 wt % of the total multiphase composition), preferably under homogenizing conditions.

A hydrophilic gel is prepared separately by dissolving at least one viscosity-enhancing, water-soluble polymer (2-5 parts by weight) in water (95-98 parts by weight). This gel (20-30 wt % of the total multiphase composition) is then mixed with the water-in-silicone emulsion to provide a dispersion in which the gel is dispersed in the water-in-silicone emulsion. Thus, two distinct water phases are produced: one in the bulk gel and a second, in the water droplets of the water-in-silicone emulsion.

The final multiphase composition (the five phase emulsion) is then obtained by adding to this dispersion effective amounts of oil or liquid crystal (about 1 to about 10 wt % of the total multiphase composition) and perfluoropolyether (about 0.5 to about 3 wt % of the total multiphase composition).

It should be apparent to one of ordinary skill that various other ingredients, both lipid-soluble or water-soluble, may be incorporated in to the multiphase composition, including, but not limited to, other lubricating gels, protein extracts, humectants, preservatives, vitamins and the like.

Also, as stated previously, the gel phase component of the resulting multiphase composition is acid-neutralized. Preferably, the neutralizing agent is selected from an amine base, such as triethanolamine, tris(hydroxymethyl)aminoethane, ethylenediamine or mixtures thereof.

5.1.3 Example Three

By following either of the procedures described above, a stable multiphase composition, having the following ingredients, is prepared (percentages in parenthesis are proportions of the specific ingredient by weight of the total multiphase composition):

| Ingredient | (%) | CFTA Name |
|---|---|---|
| WATER-IN-SILICONE PHASE | | |
| a 1.5% aqueous Solution of Hypan SS-201 | (11.25) | Acrylamide Copolymer |
| DC Q2-1403 | (15.0) | Dimethicone and Dimethiconol |
| DC Q2-3225C | (5.0) | Cyclomethicone and Dimethicone Copolyol |
| HYDROPHILIC GEL PHASE | | |
| 3.5% CARBOPOL 940 | (25.25) | Carbomer |
| Lubrajel MS | (18.0) | Polyglyceryl-methacrylate and Propylene glycol |
| Germall 115 | (0.3) | Imidazolidinyl Urea |
| Disodium EDTA | (0.1) | Disodium EDTA |
| Methylparaben | (0.1) | Methylparaben |
| TEA | (1.0) | Triethanolamine |
| PERFLUOROPOLYETHER PHASE | | |
| Fomblin HC/25 | (2.0) | Perfluoromethyl-isopropyl Ether |
| LIQUID CRYSTAL PHASE | | |
| Licritherm 789 | (5.0) | Cholesteric Cosmetic Esters; optional "actives" such as Vitamin A Palmitate and 7-Dehydrocholesterol may also be present |

5.1.4 Photomicroscopy

Figure 1:
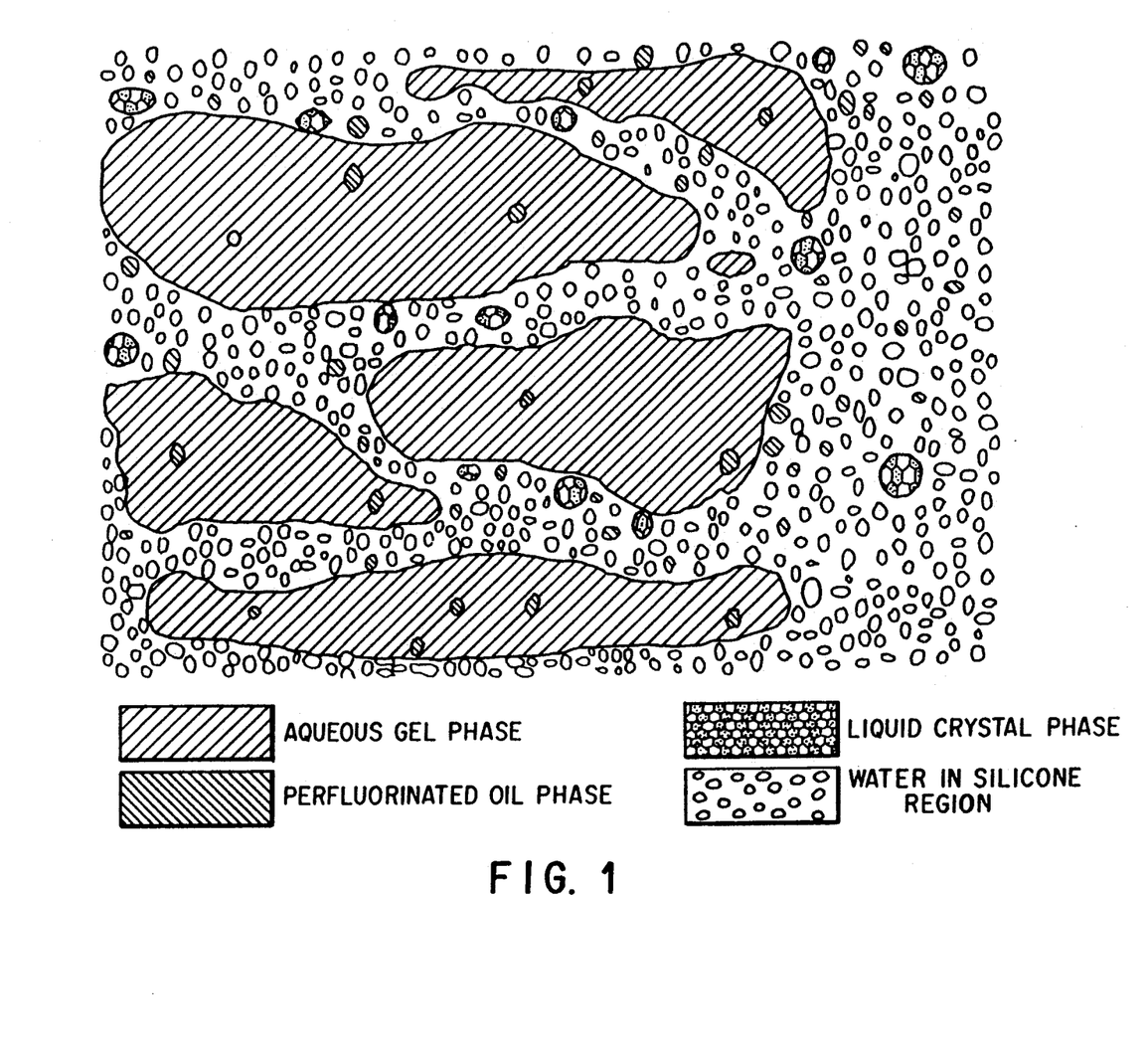
FIG. 1. Schematic of Photomicrograph of a Five-Phase Emulsion Obtained by the Method of the Present Invention.
Figure 2:
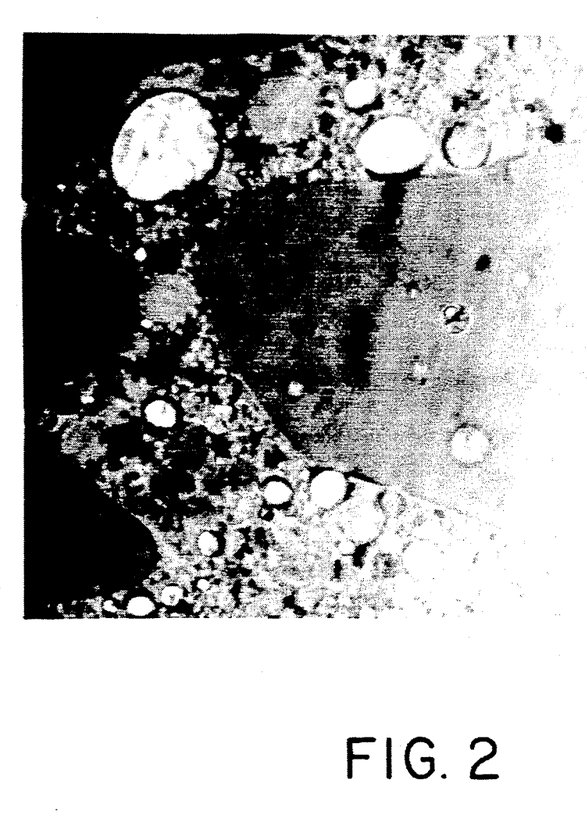
FIG. 2. A Photomicrograph of a Five-Phase Emulsion of the Present Invention.

After staining the aqueous gel phase with a water-soluble dye (FD&C Blue #1), microscopy with cross polarizers was used to determine the integrity and identify the location of the liquid crystals within the multiphase emulsion. Photomicrographs were then used to examine the four immiscible dispersed regions. These four regions were: (1) the water droplets in the hydrophobic silicone fluid region which remained unstained by dye, (2) the aqueous gel region which stained blue, (3) the Fomblin "droplets", and (4) the liquid crystalline "droplets". It was observed that the size of the water droplets fell generally in the range of about 0.01 to about 3000 microns in diameter, with a majority of such droplets falling in the size range of about 0.1 to about 500 microns in diameter. (See, FIG. 2).

5.1.5 Number of Water Phases

Whereas the water in the aqueous gel phase was stained blue, the water in the water/silicon emulsion did not stain blue. After vigorous mixing, the water in the silicon emulsion remained largely unstained. Only the mechanical shear provided by vigorous mixing provided enough force to transport the dye in the aqueous gel phase to the water emulsion with the silicon. This suggests that the multiphase emulsion contains two distinct aqueous phases. Thus, the multiphase emulsion consists of five phases.

5.1.6 Dilution Experiments—Location of Silicone Phase

The location of the five phases was experimentally determined by modifying phase composition.

One batch of the product containing 0.05% FD&C #1 dye dissolved in the aqueous gel phase, No. PAR 2058/1, served as the control with dye.

A second batch of product, PAR 2058/2, containing 0.05% FD&C #1 dye dissolved in the aqueous gel phase, lacked emulsifiers but contained the solvents found in the emulsifiers (water in the case of the Hypan to make a 1.5% aqueous solution of Acrylamide Copolymer) solution and DC 345 (Cyclomethicone) in the case of DC-3225C (Cyclomethicone and Dimethicone Copolyol). The lack of emulsifiers guaranteed an aqueous external phase.

A third batch of product, PAR 2058/3, containing 0.05% FD&C Blue #1 was dissolved in the Hypan phase, but was otherwise a normal product mixture.

A fourth batch of product, PAR 2058/4, contained 0.15% FD&C Blue #1 in the water/silicon emulsion which was dissolved in the Hypan.

One gram of each of the above batches was shaken vigorously with nine grams of water or five centistokes dimethicone diluent in a capped test tube. The liquid mixture was then observed to see if the product had dispersed in the diluent solvent or not. The observations are tabulated below in Table 1.

TABLE 1

| | SAMPLE DISPERSED IN: | |
|---|---|---|
| SAMPLE | WATER | SILICONE: |
| PAR 2058/1 | (−) | (+) |
| PAR 2058/2 | (+) | (−) |
| PAR 2058/3 | (−) | (+) |
| PAR 2058/4 | (−) | (+) |

The results for PAR 2058/1, PAR 2058/3, and PAR 2058/4 indicate an external phase of the product is primarily silicone in nature. As a control experiment, to confirm that the silicones of the product do not simply repel the diluting water, PAR 2058/2 was made without emulsifiers, ensuring an aqueous external phase. PAR 2058/2 readily dispersed in water indicating that silicones in the product do not simply repel the diluting water. To repel water, the silicones must be positioned in the external phase and this required the activity of the emulsifiers.

All product samples contained a high level of dye. In all the samples that were not water-dispersable the supernatant water was much more lightly stained relative to the water-dispersable sample. This suggests that only stained water droplets present at the water-silicone interface can actually color the supernatant water.

In the case where product was made without water-soluble dye, it was found that addition of water-soluble dye to the product did not color it. Photomicrographs reveal little beads of dye solution at the external phase of the product. This indicates that silicone is in the external phase of the product.

5.1.7 Determination of Positions of Remaining Phases

To determine the relative positions of the other phases the following mixtures were made and shaken vigorously. The observations are summarized below:

1. A mixture of Silicones (Q2-1403) in Water and Fomblin resulted in a three layer separation with some Fomblin at the Water/Silicone interphase and some Silicone at the Water/Fomblin interphase.

2. A mixture of Fomblin in Water and Liquid Crystal formed a three layer separation wherein the Liquid Crystal was found only at the Water/Fomblin interphase.

3. A mixture of silicones (Q2-1403) in Water and Liquid Crystal formed a two layer separation. The upper layer was silicone with Liquid Crystal dispersed throughout. There was some gravitational settling of the Liquid Crystal in the upper layer while the lower aqueous liquid layer was clear.

These observations are consistent with the photomicrograph data on the product. First, silicon forms a continuous phase in the product. Second, within the silicone is a water phase in the form of an emulsion with the silicone which is quite stable. Third, there is another water phase present as a coarse gel dispersion stabilized by electrostatic repulsion since it contains very high levels of polyanions resulting in a very anionic surface. Fourth, there is a liquid crystal phase which is dispersed in the silicone phase as well as at the various other interfaces. Fifth and lastly, there is a Fomblin phase since it is extremely non-miscible with the other components of the product.

5.2 TEST OF CHANGES DUE TO PRODUCT PRESSURE SENSITIVITY

When subjected to shear forces by manually stirring it with a rod, or by vigorous mixing, or during its application to the skin, the product has been observed to dull, to become more gel-like, and to thicken. These effects are immediately reversed when the product is allowed a rest from the stress. In the nonstressed state, the product is more flowable and creamy. When the product is stressed by shear forces, it is postulated that it undergoes a phase inversion. During this time the coarse aqueous gel phase which is the bulk of the product, becomes the continuous phase and reverses roles with the silicone/water phase.

Consistent with this phase inversion, it was found that the pH of the "resting" emulsion had a value of about 5.5±0.2 and was, furthermore, unstable, indicative of an emulsion with a non-water continuous phase. However, under vigorous stirring or "stressed" conditions, the pH goes up to about 6.25–6.5, a value that is very similar to the pH of the unemulsified gel phase. On sitting, the pH returns to a value of about 5.5.

5.3 TEST FOR SHORT AND LONG-TERM MOISTURIZATION

Moisturization of the skin was measured using a Gas Bearing Electrodynamometer (GBE) according to Maes D. *Int. J. Cosm. Sci.* 5:189–200 (1983). The GBE measures skin softness by moving a probe parallel to the skin under the same force and measuring its displacement. The difference between readings taken before and after treatment allows a percent improvement in skin moisturization/softness to be calculated.

Figure 3:
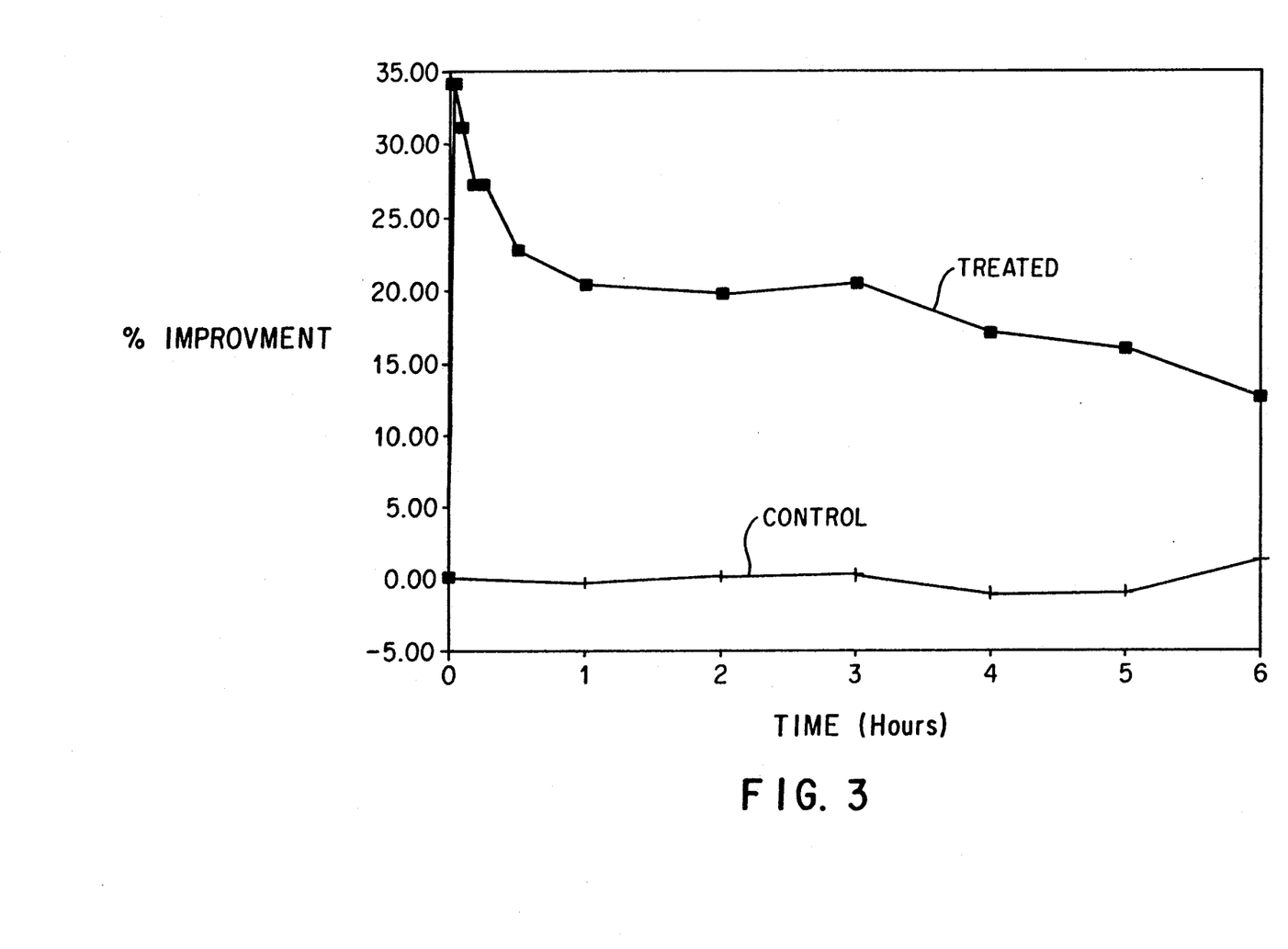
FIG. 3. Graphical Illustration of Short-Term Skin Moisturization with Five-Phase Emulsion Versus Control FIG. 4. Graphical Illustration of Long-Term Skin Moisturization with Five-Phase Emulsion

Referring now to FIG. 3, the product was applied to skin and found to increase the skin moisturization immediately by 34%. After six hours of exposure to the product, the skin remained 13% more moisturized than untreated skin.

Figure 4:
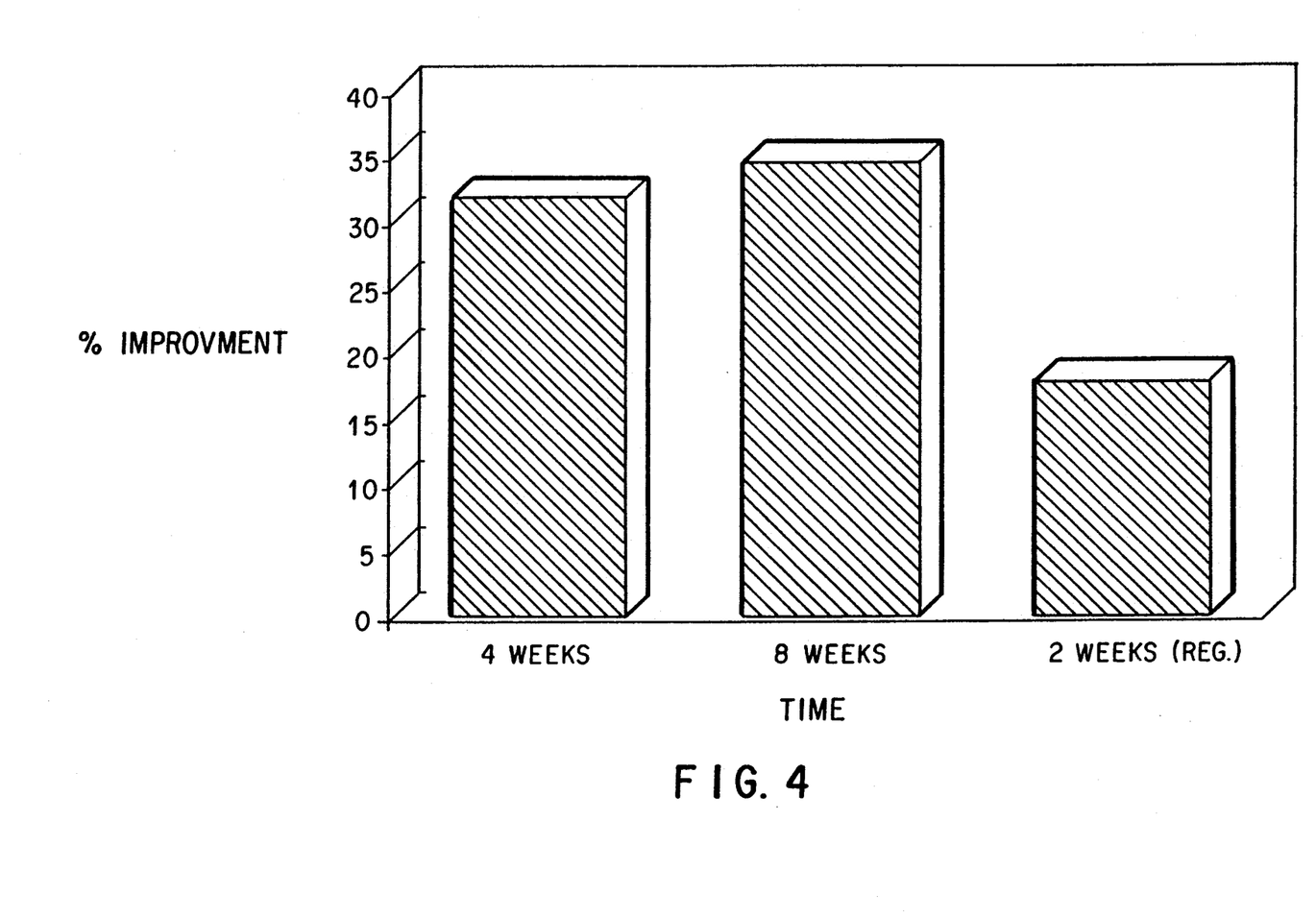

Long term (e.g., eight weeks) use of the product on the skin caused a 35% improvement in skin moisturization over untreated skin as can be gleened from the results depicted in FIG. 4. Despite a two week discontinuation of product use, the skin was 18% more moisturized than untreated skin.

It should be apparent to those skilled in the art that other methods not specifically disclosed in the instant specification are, nevertheless, contemplated thereby. Such other methods are considered to be within the scope and spirit of the present invention. Hence the invention should not be limited by the description of the specific embodiments disclosed herein but only by the following claims.

What is claimed is:

1. A method of forming a stable, multiphase composition comprising:
   (a) mixing an aqueous solution of a water-soluble polymeric emulsifier, a silicone-based emulsifier and an oleophobic, hydrophobic silicone fluid in amounts effective to form a stable water-in-silicone emulsion;
   (b) mixing said water-in-silicone emulsion with a hydrophilic gel comprising a homogeneous mixture of water and a sufficient amount of at least one viscosity-enhancing, water-soluble polymer, said emulsion and gel being combined in amounts effective to form a dispersion in which said gel is dispersed in said emulsion; and
   (c) adding to said dispersion a thermotropic liquid crystal and a perfluoropolyether in amounts effective to form a stable, multiphase composition comprising a continuous phase of silicone fluid and independent, polydisperse phases of water, gel, liquid crystal and perfluoropolyether.

2. The method of claim 1 in which each of the process steps is carried out under homogenizing conditions.

3. A method of stabilizing a multiphase composition in which independent phases of water, a hydrophilic gel comprising a homogeneous mixture of water and a sufficient amount of at least one viscosity-enhancing water-soluble polymer, a liquid crystal and a perfluoropolyether are dispersed in a continuous phase of silicone fluid comprising adding an effective amount of a water-soluble polymeric emulsifier, or an aqueous solution thereof, to an aqueous mixture of an oleophobic, hydrophobic silicone fluid and a silicone-based emulsifier to form a stable water-in-oil emulsion and adding to said emulsion gel, said liquid crystal and perfluoropolyether components of said multiphase composition.

4. The method of claim 1 or 3 in which said multiphase composition is further characterized as being capable of undergoing a temporary phase inversion upon exposure to external pressure, shear or other form of stress.

5. The method of claim 1 or 3 in which said multiphase composition is further characterized as being capable of providing high initial moisturization followed by lower sustained moisturization.

6. The method of claim 1 or 2 in which said gel further includes releasable bioavailable water-soluble ingredients.

7. The method of claim 1 or 3 in which an oil capable of carrying and releasing lipid-soluble ingredients is used in place of said liquid crystal.

8. The method of claim 7 in which said oil is non-surface active and non-detergent.

9. The method of claim 7 in which said oil comprises a material selected from the group consisting of long-chain saturated fats, waxes and cholesteric molecules.

10. The method of claim 1 or 3 which further comprises dispersing in said multiphase composition a preselected amount of an oil capable of carrying and releasing lipid-soluble ingredients.

11. The liquid crystal phase according to claims 1 or 3 in which said liquid crystal comprises cholesteric esters.

12. The method of claim 1 or 3 in which said water-soluble polymeric emulsifier is a material selected from the group consisting of HYPAN SS-201, CARBOPOL 940, STABILEZE 06 and a copolymer of $C_{10-30}$ alkyl acrylates and at least one monomer of a material selected from the group consisting of acrylic acid, methacrylic acid and one of their simple esters, crosslinked with an alkyl ether of sucrose or pentaerythritol.

13. The method of claim 1 or 3 in which said water-soluble polymeric emulsifier is a carbomer, a polyacrylic acid, a polyacrylamide, an alginated-based polymer, a cellulosic thickener, a locust bean polymer, polyglycerylmethylacrylate or mixtures thereof.

14. The method of claim 1 or 3 in which said oleophobic, hydrophobic silicone fluid comprises dimethicone.

15. The method of claim 1 or 3 in which said silicone-based emulsifier comprises dimethicone copolyol.

16. The method of claim 1 or 3 in which said perfluoropolyether comprises a perfluoropolyalkyl ether.

17. The method of claim 1 or 3 in which said gel is acid neutralized.

18. The method of claim 17 in which said neutralization is effected with a base.

19. The method of claim 18 in which said base is an amine selected from the group consisting of triethanolamine, tris(hydroxymethyl)aminoethane, ethylenediamine and mixtures thereof.

20. The method of claim 1 or 3 in which said polydisperse water phase exists as droplets having a diameter falling in the range of about 0.01 to about 3000 microns.

21. The method of claim 1 or 3 in which said polydisperse water phase exists as droplets having a diameter falling in the range of about 0.1 to about 500 microns.

22. The method of claim 1 or 3 in which said polydisperse gel phase exists as droplets having a diameter falling in the range of about 0.01 to about 3000 microns.

23. The method of claim 1 or 3 in which said polydisperse gel phase exists as droplets having a diameter falling in the range of about 0.1 to about 500 microns.

24. The method of claim 1 or 3 in which said perfluoropolyether has a molecular weight falling in the range of about 1,000 to about 10,000.

25. The method of claim 1 or 3 in which said amounts of the various components of said multiphase composition are such that the continuous phase of silicone fluid comprises about 10 to about 20 weight percent (wt %) of said multiphase composition and independent, polydisperse phases of water comprises about 5 to about 15 wt %, gel comprises about 35 to about 55 wt %, liquid crystal comprises about 1 to about 10 wt % and perfluoropolyether comprises about 0.5 to about 3 wt % of said multiphase composition.

26. A method of forming a stable, multiphase composition comprising:
(a) mixing an aqueous solution of a water-soluble polymeric emulsifier including a polyacrylamide block copolymer, a silicone-based emulsifier including dimethicone copolyol and an oleophobic, hydrophobic silicone fluid including dimethicone in amounts effective to form a stable water-in-silicone emulsion;
(b) mixing said water-in-silicone emulsion with a hydrophilic gel comprising a homogeneous mixture of water and a sufficient amount of at least one viscosity-enhancing, water-soluble polymer including carbomer, said emulsion and gel being combined in amounts effective to form a dispersion in which said gel is dispersed in said emulsion; and
(c) adding to said dispersion an oil or a thermotropic liquid crystal including cholesteric esters and a perfluoropolyether including perfluoromethylisopropyl ether in amounts effective to form a stable, multiphase composition comprising a continuous phase of silicone fluid and independent, polydisperse phases of water, gel, liquid crystal and perfluoropolyether.

27. A method of forming a stable, multiphase composition comprising:
(a) mixing an aqueous solution of a water-soluble polymeric emulsifier including a block copolymer of acrylamide and acrylonitrile, a silicone-based emulsifier including a mixture of cyclomethicone and dimethicone copolyol and an oleophobic, hydrophobic silicone fluid including a mixture of dimethicone and dimethiconol in amounts effective to form a stable water-in-silicone emulsion;
(b) mixing said water-in-silicone emulsion with a hydrophilic gel comprising a homogeneous mixture of water and a sufficient amount of a viscosity-enhancing, water-soluble polymer including carbomer, a second hydrophilic polymer including polyglycerylmethacrylate and an acid neutralizing amount of an amine base, said emulsion and gel being combined in amounts effective to form a dispersion in which said gel is dispersed in said emulsion; and
(c) adding to said dispersion an oil or a thermotropio liquid crystal including cholesteric esters and cholesterols, in which a vitamin is incorporated in said liquid crystal, and a perfluoropolyether including perfluoromethylisopropyl ether in amounts effective to form a stable, multiphase composition comprising a continuous phase of silicone fluid and independent, polydisperse phases of water, gel, liquid crystal and perfluoropolyether.

* * * * *